United States Patent
Ng et al.

[11] Patent Number: 6,162,171
[45] Date of Patent: Dec. 19, 2000

[54] ROBOTIC ENDOSCOPE AND AN AUTONOMOUS PIPE ROBOT FOR PERFORMING ENDOSCOPIC PROCEDURES

[75] Inventors: Wan Sing Ng, Blk 827, #06-278 Jurong West Street 81, Singapore 640827; Soo Jay Louis Phee; Choen Francis Seow, both of Singapore, all of Singapore

[73] Assignee: Wan Sing Ng, Mimosa Walk, Singapore

[21] Appl. No.: 09/207,320

[22] Filed: Dec. 7, 1998

[51] Int. Cl.⁷ .................................................. A61B 1/008
[52] U.S. Cl. ........................ 600/141; 600/101; 600/114; 600/152
[58] Field of Search ................................. 600/101, 102, 600/114, 139, 152, 141; 901/1, 22; 318/568.12; 73/865.8, 866.5; 604/95

[56] References Cited

U.S. PATENT DOCUMENTS

| | | | |
|---|---|---|---|
| 3,665,928 | 5/1972 | Del Guercio | 604/95 |
| 3,895,637 | 7/1975 | Choy | 604/95 |
| 4,148,307 | 4/1979 | Utsugi | 600/116 |
| 4,207,872 | 6/1980 | Meiri et al. | 600/115 |
| 4,769,006 | 9/1988 | Papantonakos | 604/95 |
| 4,934,786 | 6/1990 | Krauter | 385/118 |
| 5,345,925 | 9/1994 | Allred, III et al. | 600/114 |
| 5,398,670 | 3/1995 | Ortiz et al. | 600/114 |
| 5,531,664 | 7/1996 | Adachi et al. | 600/149 |
| 5,595,565 | 1/1997 | Treat et al. | 600/114 |
| 5,662,587 | 9/1997 | Grundfest et al. | 600/114 |
| 5,906,591 | 5/1999 | Dario et al. | 604/95 |

*Primary Examiner*—John P. Leubecker
*Attorney, Agent, or Firm*—Sughrue, Mion, Zinn, Macpeak & Seas, PLLC

[57] ABSTRACT

A robotic endoscope for performing endoscopic procedures in a tubular organ comprising: (a) a plurality of segments, connected together by a plurality of flexible articulated joints, having a distal end; (b) a plurality of flexible linear actuators attached, skewed sideways with respect to the longitudinal axis of said robot, circumferentially round each segment; (c) a central cavity running longitudinally through said robotic endoscope which houses a plurality of optical fibres, a water/air hose, an instrumentation channel and a plurality of electrical wires associated with an imaging means being mounted at the distal end of the robotic endoscope; and (d) a network of tributary channels for the distribution of pressure to said linear actuators. The present invention is also applicable to an autonomous pipe robot.

20 Claims, 5 Drawing Sheets

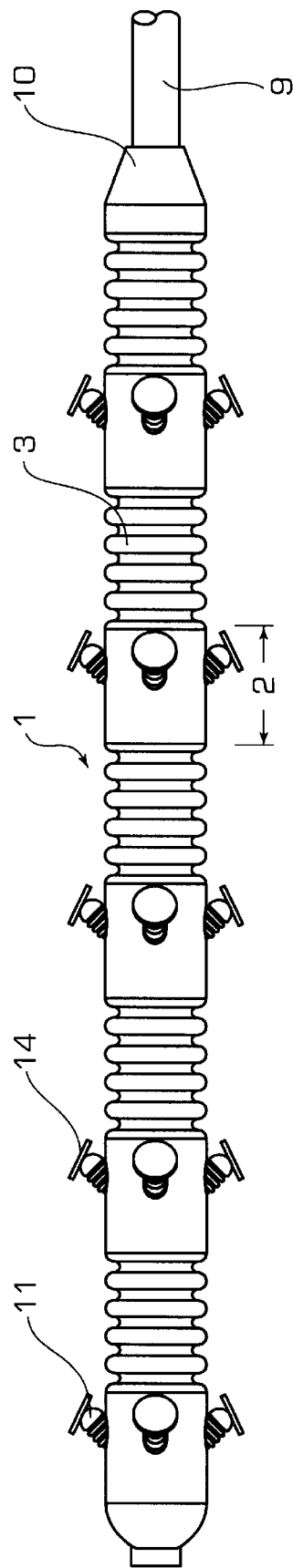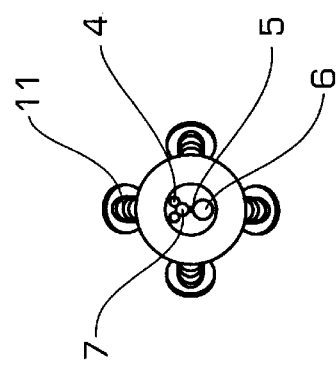

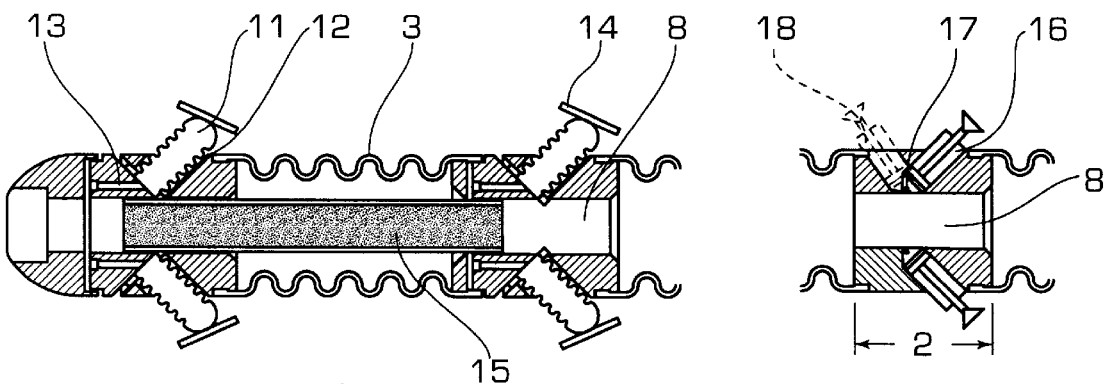
FIG. 3
FIG. 4
FIG. 5(a)
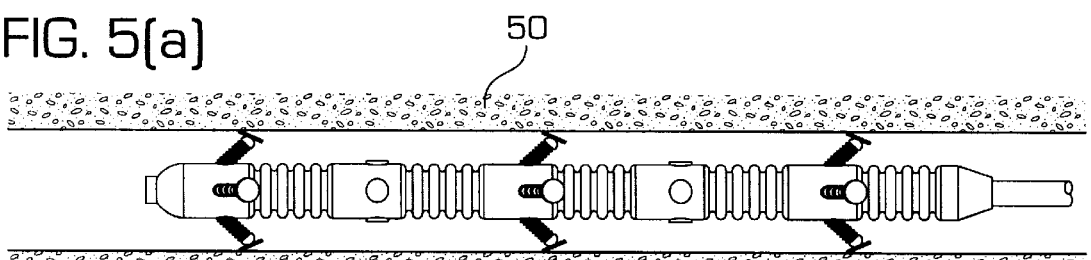
FIG. 5(b)
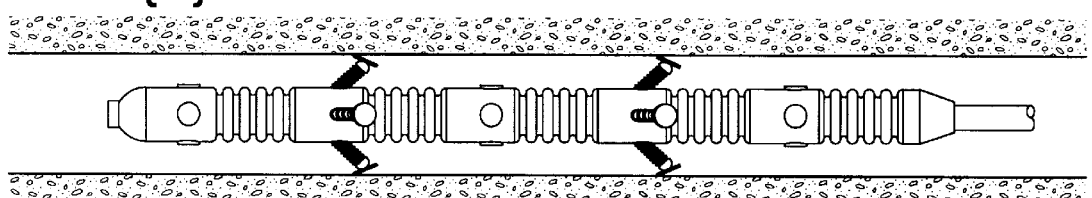
FIG. 5(c)
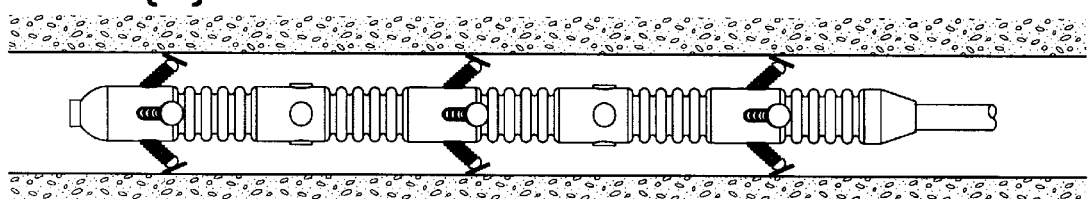
FIG. 5(d)
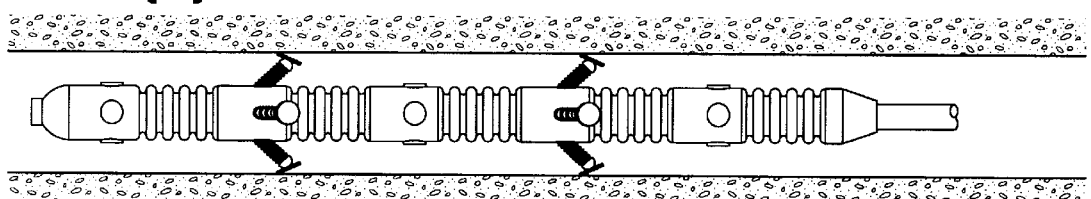

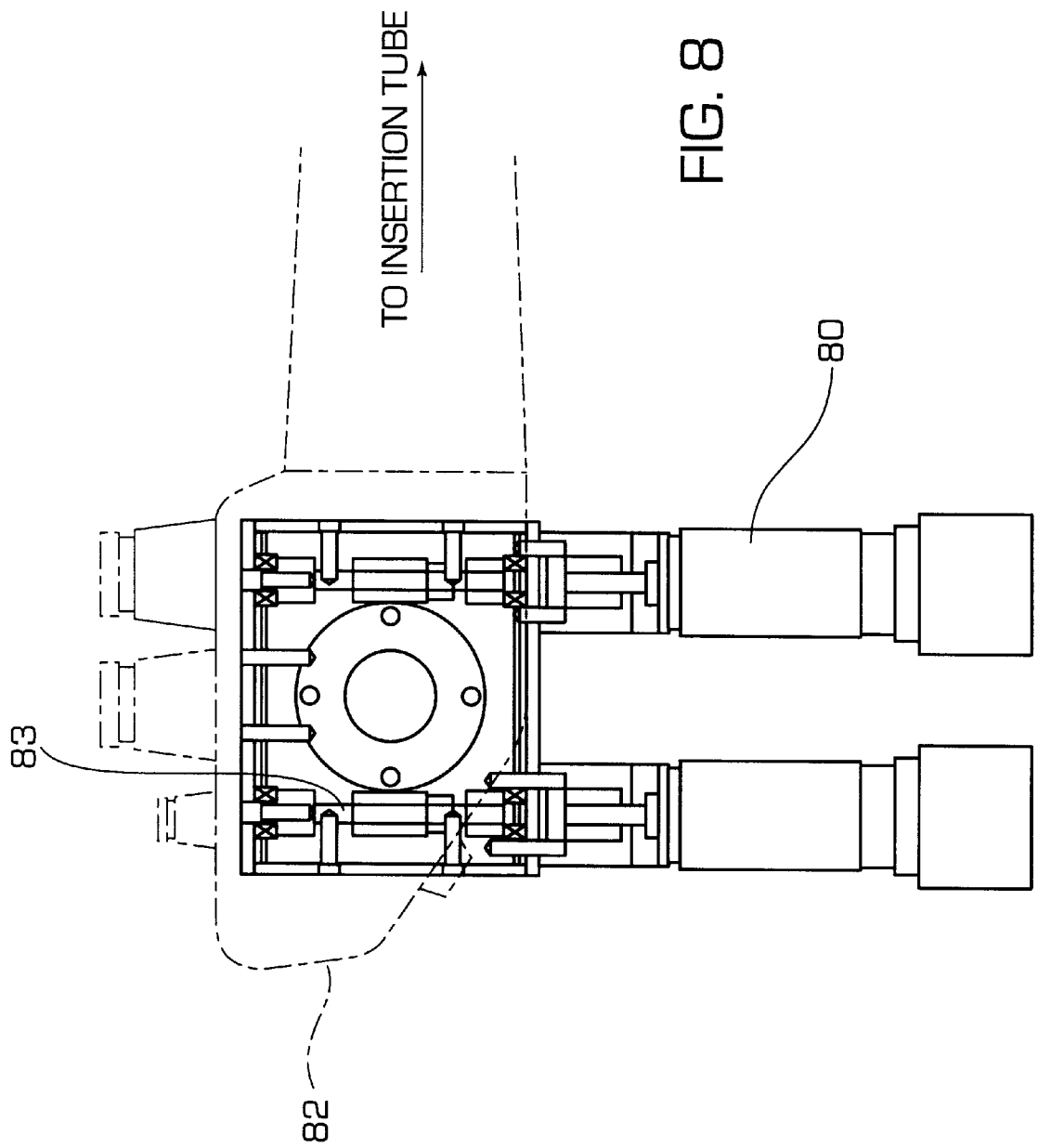

ROBOTIC ENDOSCOPE AND AN AUTONOMOUS PIPE ROBOT FOR PERFORMING ENDOSCOPIC PROCEDURES

BACKGROUND OF THE INVENTION (a) Field of the Invention

The present invention generally relates to a robotic endoscope for performing inspection and endoscopic procedures, in particular, to a self-propelled tubular robot and an autonomous pipe robot capable of advancing within an elongated passage, either a straight or bent passage, having a rigid or elastic, tubular wall.

(b) Description of the Prior Art

Endoscopes are useful medical device for inspecting and examining the interior of certain human organs that are otherwise inaccessible to a physician's examination. An endoscopic examination, like colonoscopy, is a procedures requiring very demanding techniques. It is a medical art to coax an almost two metres long flexible tube around a tortuous colon whilst causing minimal discomfort and yet performing a thorough examination.

Most experienced endoscopists use similar endoscopic techniques. Air is pumped into the colon to distend it and aid insertion of the flexible tube. The insertion force on the device must be gentle to avoid stretching the colonic wall or mesentery which can cause pain or perforation to the wall. The colonoscope is advanced, by the pushing action of the endoscopist's hand, to the caecum under direct endoscopic vision made available to the endoscopists by optical fibres or CCD cameras. The lumen should be kept always in view so that little or none of the operation is performed blind. A variety of "in-and-out" manoeuvres are used to "accordion" the colon on the colonoscope, keeping the colonoscope as free of loops as possible. However, pushing is not the only action involved. Considerable skill is required to pull, wriggle and shake the colonoscope at the distal end. The patient's abdomen may be pressed to minimize looping and discomfort. In a difficult colon, special manoeuvres (like reducing the "alpha loop" in the sigmoid colon) are used to pass the sharply angulated sigmoid/descending colon junction. Torquing of the colonoscope is also required in such a scenario.

The detailed examination of the mucosa is performed both as the colonoscope is introduced and when it is slowly removed from the caecum. If the colonoscope is kept free of loops, the tip responds well and the examination is facilitated. This is especially true if a therapeutic procedure (such as polypectomy) is to be undertaken, because large, redundant loops of the colonoscope can make control of the tip very difficult. Sometimes, the endoscopist may "jiggle" the scope to pleat the colon onto the shaft of scope. This involves rapid up/down or side-to-side movements of the scope. The main purpose of jiggling is to shorten the part of the insertion tube which is in the body. This keeps it straight.

The basic act of manoeuvring the colonoscopic tip around the many bends of the colon requires years of practice and training. During the operation, the lumen may disappear from the surgeon's sight leading to a "red-out" when the tip is against the colonic wall or worse; a "white-out" when the tip stretches the colonic wall. When this happens, an inexperienced endoscopist may be disorientated and has difficulty looking for the lumen. Colonic perforation may consequently occur. Furthermore, abrupt movements of the scope may result in tearing of the inner wall of the colon, which may in turn lead to excessive bleeding. There are also instances when pushing in the scope does not result in advancement of the distal end. Rather, loops are formed which may result in over distension of the colonic walls. The present colonoscope also requires the endoscopist to hold the control device with one hand leaving only one hand to push or pull the insertion tube. Too much torquing of the insertion tube may result in loops which may complicate matters further. Besides being cumbersome, holding up the control device for prolonged periods of time is tiring for the endoscopist.

The colonoscopy procedure depends very much on the skills of the endoscopist. A more experienced endoscopist will perform a more thorough, less painful operation in a shorter time than an inexperienced endoscopist. A skilled endoscopist will normally have little problems traversing the colonoscope right up to the caecum of a "normal" colon. However, there will be difficulties advancing the colonoscope through some "problematic" colons. This happens when encountering very acute or fixed bends. Further pushing of the colonoscope at this point will only distend the walls of the distal colon. Distortion of the colonic shape and profile due to previous surgery may add to this problem. A self-propelled robotic endoscope with a traversing mechanism at its distal end will solve many locomotion problems unlike the problematic pushing format of conventional colonoscopes.

In the chemical and oil industries, conducting characterization and inspection activities within piping systems is critical to decontamination, dismantlement and maintenance activities. Current technologies for inspection of large piping systems exist. However, the ability to accurately characterize and inspect small-diameter piping systems are rare. Small-diameter pipes (diameters less than 3 inches) are generally connected together to form 3-dimensional structures made up of horizontal and vertical pipes. Inspecting of such piping systems would require a self-propelled in-pipe robot not only capable of advancing against gravity but also capable of traversing through acute bends. The robot's objective is to send back images of the inner walls of the pipes as it advances into the pipes. It must also be able to proceed in a desired direction when it reaches a junction with two or more alternative routes.

SUMMARY OF THE PRESENT INVENTION

Accordingly, the present invention relates to a robotic endoscope for performing endoscopic procedures in a tubular organ comprising: (a) a plurality of segments, connected together by a plurality of flexible articulated joints, having a distal end; (b) a plurality of flexible linear actuators attached, skewed sideways with respect to the longitudinal (or diametral) axis of said robot, circumferentially round each segment; (c) a central cavity running longitudinally through said robot which houses a plurality of optical fibres, a water/air hose, an instrumentation channel and a plurality of electrical wires associated with an imaging means being mounted at the distal end of the robot; and (d) a network of tributary channels for the distribution of pressure to said linear actuators.

It is an object of the present invention to provide a robotic endoscope and an autonomous pipe robot capable of advancing in an elongated passage having rigid or elastic, tubular wall, wherein a plurality of articulated joints allow the robot to conform to the different bends and curvature found in the organ of a human body.

It is yet another object of the present invention to provide a robotic endoscope and an autonomous pipe robot, wherein a plurality of flexible linear actuators are attached circumferentially round each segment and these actuators are pressure driven by pneumatics or hydraulics.

It is another object of the present invention to provide a robotic endoscope and an autonomous pipe robot, wherein a control means is provided to control the sequence by which the linear actuators are activated.

It is another object of the present invention to provide a robotic endoscope and an autonomous pipe robot, wherein the robot is capable of advancing in pipes of small diameters.

These and other features, aspects, and advantages of the present invention will become better understood with regard to the following description, appended claims, and accompanying drawings where:

BRIEF DESCRIPTION OF THE DRAWINGS

FIG. 1 is a schematically illustrated side elevation view of the present tubular robot in accordance with the present invention;

FIG. 2 is a front end view of the present tubular robot in accordance with the present invention;

FIG. 3 is a partial section view of the distal segments of the robot shown in FIG. 1;

FIG. 4 is a partial section view of another preferred embodiment of the robot in accordance with the present invention;

FIG. 5 illustrates a gait sequence which is used to locomote the present robot in accordance with the present invention;

FIG. 8 shows the sectional view of a motor in accordance with the present invention.

DESCRIPTION OF THE PREFERRED EMBODIMENT

Figure 6:
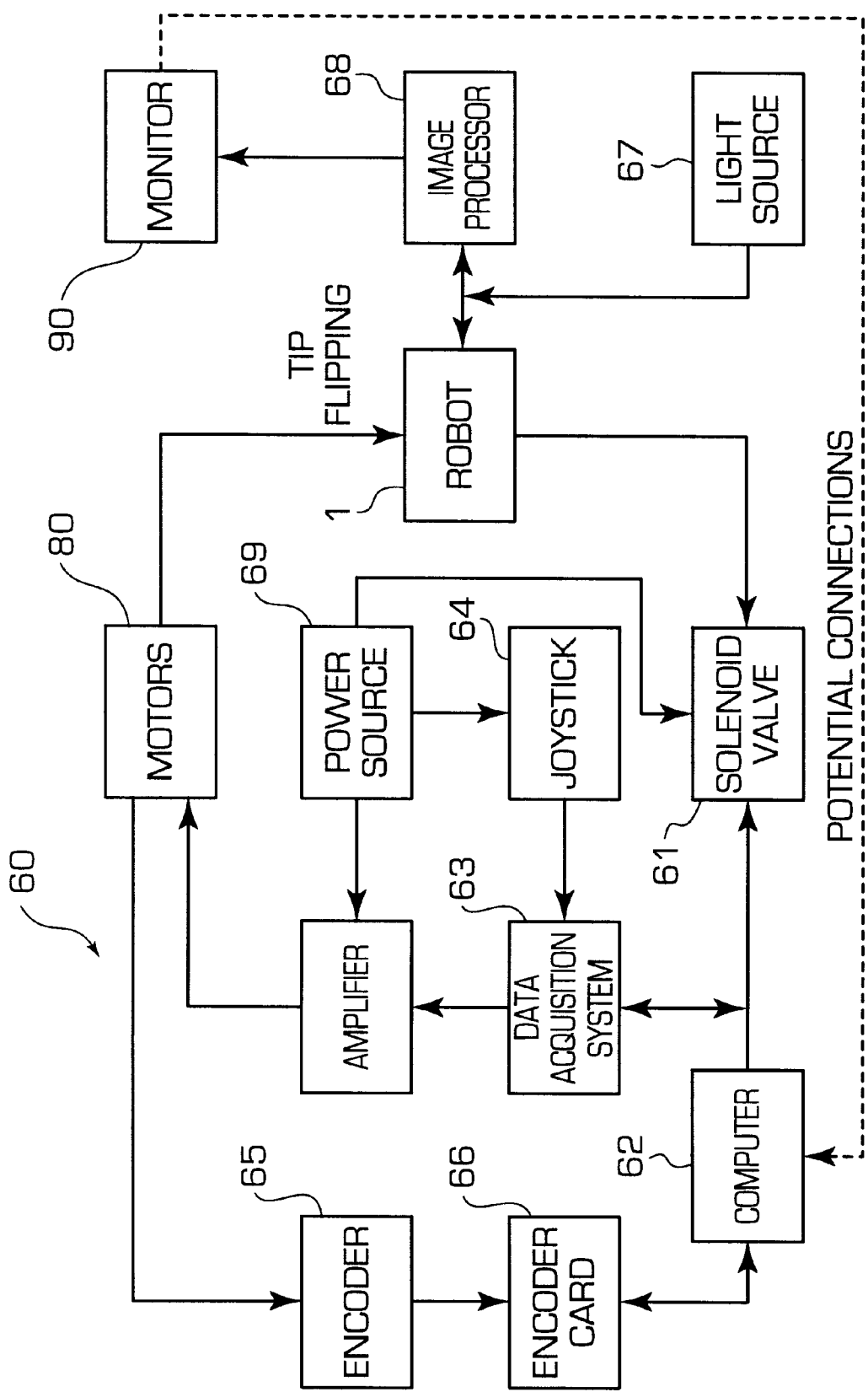
FIG. 6 shows a flow chart of a control means in accordance with the present invention.

Referring to FIG. 1, there is shown a tubular robot (1) capable of advancing in an elongated passage with rigid or elastic, tubular wall. The robot (1) comprises a plurality of segments (2), having a distal end, connected together by a plurality of flexible articulated joints (3). The articulated joints (3) provide the robot (1) to conform to the different bends and curvature found in the human organs. A plurality of hollow rubber bellows (11) are used to make the joints (3) each of which has three degrees of rotational freedom and certain degree of translational freedoms.

Referring to FIG. 2, the distal end of the segment (2) houses a plurality of optical fibres (not shown) for a light source (4), a water/air opening (5), an instrumentation channel (6) and an imaging device (7), such as an ultra-compact charge couple camera. The wires and tunings (not shown) associated with these devices (4, 6, & 7) run into the central cavity (8) of the robot (1). These wires and tunings exit the robot (1) bundled together as a tail (not shown) which connects to the last segment (10).

Referring to FIG. 3, attached circumferentially round each segment (2) is a plurality of flexible linear actuators (11). In accordance with the present invention, the plurality of the retractable rubber bellows (11) are used as the linear actuators. These actuators (11) are pressure driven by pneumatics or hydraulics. As the actuators (11) are not made from metals, the actuators (11) will not damage the delicate walls of the human organs. These rubber bellows (11) are attached, by proximal ends, to the cavities (12) in the segments (2). The bellows (11) are clamped or glued to the segments (2). They are positioned skewed sideways with respect to the longitudinal axis of the body (of the robot) with their distal ends pointing radially away from the main body (of the robot). All the bellows (11) in one segment (2) are connected to the same pressure line which runs through the central cavity (8) of the main body of the robot (1) and exits via the tail (9). Pressure is distributed evenly to the bellows (11) via a plurality of the tributary pressure channels (13) in the segment (2). When high pressure, from an external source, is introduced through the channels (13), the connected bellows (11) will extend longitudinally. Conversely, when low pressure (below atmospheric pressure) is introduced, the bellows (11) will retract into the cavities (12) in the segment (2). Locomotive force is produced as the bellow (11) extends to push against the internal walls of the organ. Being flexible radially, the bellow (11) may bend towards the robot's 1 main body when it comes into contact with the organic walls. Further extension of the bellow (11) will continue to bring about forward locomotive forces. This collapsible mechanism is a safe-guard against puncturing and perforation of the delicate walls. To prevent slippage at the point of contact, the bellow (11) may be padded as shown by (14) to increase the surface area of contact.

FIG. 6 shows a flowchart of a control means (60) which controls the sequence by which the bellows (11) are extended or retracted. Each set of bellows (11) within one segment (2) or even each individual bellow (11) may be activated independently. In accordance with the present invention, the user operates the robot (1) via a graphical user interface developed using a computer program run on a desktop PC (62). This program is responsible for most of the control functions of the robot (1). With the aid of a data acquisition system (63), it controls the type of gait sequence to be used, its speed and the robot's ability to insufflate or deflate the colon. This is done by opening or closing independent solenoid valves (61) which allow air pressure or vacuum to pass into the respective actuators in the robot (1). The steerable distal head of the robot (1) is actuated by 2 DC motors (80). The user controls a 2-axis joystick (64) to indicate the position he wants the head to bend to. The changes in the voltages of the corresponding potentiometers are sensed by the data acquisition system (63). The computer program then processes this data into encoder (65) readings corresponding to the desired position. An analogue voltage signal is passed via the data acquisition system (63) to operate the motors (80). The computer program will ensure that the polarity of the input voltage will cause the motor (80) to turn in the desired direction. The program also constantly reads the actual encoder (65) reading via a 3-axis quadrature encoder (65) and counter card (66). When the encoder (65) reading comes into a range close to the desired reading set by the joystick (64), the program will cause the motor (80) to decelerate and finally stop. If the motor (80) overshoots this range, the program will cause the motor (80) to adjust itself back into the range. The monitory the (90), light source (67) and the image processor (68) are equipment required to retrieve the robot's endoscopic view.

Figure 7:
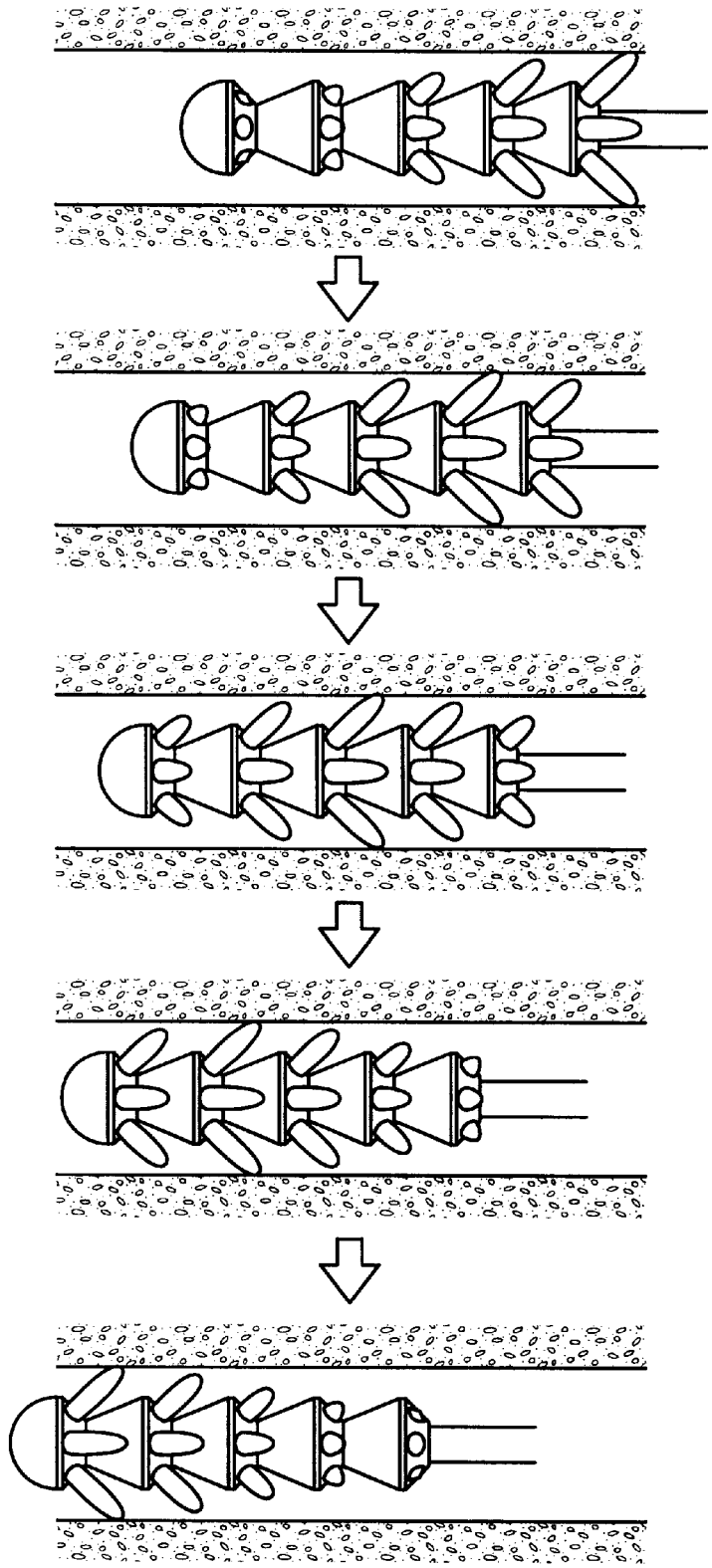
FIG. 7 shows a gait in which the sets of bellow actuators, in accordance with the present invention, are activated antagonistically.

FIG. 5 illustrates a gait sequence which is used to locomote the present robot (1) and FIG. 7 shows a gait (50) in which the sets of bellow actuators (11) are activated antagonistically in accordance with the present invention. In the present embodiment, the robot (1) can be made to locomote using a plurality of various types of gaits (50). As shown in FIG. 5, there is shown how alternate sets of bellows (11) are sequenced to extend and retract simultaneously to bring about forward locomotion. Depending on the number of segments (2) in the robot (1), the plurality of gaits (50) may be designed for optimum performance relating to speed, ability to advance against gravity or ability to advance through difficult bends. To extract the robot (1) from the tubular organ, all bellows (11) are retracted. The user then pulls out the robot 1 holding onto the proximal tail (9) end. In accordance with the present invention, the movement of the robot (1) depends solely on the pushing force of the bellows actuators (11). The pressurized air is introduced into the robot (1), the bellow actuators (11) will start to inflate, growing longitudinally until it touches the colon walls at 45 degrees. If the friction is arranged to be large enough so that the point of contact does not slide, there will be a resultant force that pushes the robot (1) forward. When a vacuum is introduced instead, the bellow (11) would collapse such that their tips touch their bases. Depending on the control means (60), different bellow actuators (11) can be inflated or deflated at different times. This results in many different types of locomotive gaits (50) which propels the robot (1) forward.

In accordance with the present invention, the distal end of the robot (1) is steerable like a conventional endoscope. This is to facilitate positioning of surgical tools and more precise inspection activities. FIG. 8 illustrates the gear box with motors (80) which is designed to turn concentric shafts of the robot (1). A plurality of lead wires connected to motors (80) located outside the robot (1) may be used to activate a steering mechanism (15) embedded in the front two segments (2). In accordance with the present invention, four lead wires (not shown) exit from the bending tube (not shown) which is situated at the distal end of the robot (1). These wires are placed 90 degrees apart. To enable the robot's head to flip, one or two wires must be pulled while the wires opposite be released. The greater the displacement of the wires, the greater the bending angle. Two wires at 180 degrees apart will form an antagonistic pair and is responsible for bending movements in one axis. The other ends of the four lead wires are connected to two concentric shafts. Each pair of wires (180 degrees apart) is connected to each shaft. By turning these shafts, pulling forces are generated on the wires which will bring about bending movements of the robot head. The control system, will determine which shaft should be turned and by how much to steer the head in a particular direction with a particular radius of curvature. As shown in FIG. 8, there is shown a gearbox with motors specially designed to turn the concentric shafts. The gearbox (82) generally consists of two worm gear sets (83) and two DC motors (80). The worm gear set (83) acts as a self locking mechanism to hold the bending head in a required position thus preventing back drive.

In another preferred embodiment of the present invention, an autonomous robot (1) capable of advancing in pipes of small diameters is also disclosed. The robot (1) comprises a plurality of rigid cylindrical segments (2) connected together by a plurality of flexible articulated joints (3). The articulated joints (3) that connect the segments (2) allow the robot (1) to conform to the different bends and curvature found in pipes. The distal end of the segment (2) houses a charge coupled camera (7) and a light source (4) responsible for the robot's (1) vision.

Referring to FIG. 4, attached circumferentially round each segment (2) is a plurality of electrically or pneumatically or hydraulically driven linear actuators (16). These linear actuators (16) are attached, by proximal ends, to cavities in the segments and are positioned skewed sideways with respect to the longitudinal axis of the body of the robot (1) with their distal ends pointing radially away from the robot (1). Locomotive force is produced as the linear actuator (16) extends to push against the internal walls of the pipe. The linear actuator (16) can also be retracted into the segments (2) such that it does not hinder locomotion when the robot (1) advances.

The linear actuator (16) may be pivoted as shown in (17) at its proximal end so as to enable it to swivel to face the opposite direction (as shown in) (18) to bring about locomotion in the reversed direction.

The control means (60) controls the sequence by which the linear actuators (16) are activated. Each set of linear actuators (16) or even each individual linear actuator (16) can be activated independently. The robot (1) in accordance with the present invention can be made to locomote using a plurality of various types of gaits (50). As mentioned earlier, FIG. 5 illustrates how alternate sets of linear actuators (16) are sequenced to extend and retract simultaneously to bring about forward locomotion. The plurality of gaits (50) may be designed for optimum performance relating to speed, ability to advance against gravity or ability to advance through difficult bends. The central cavity (8) in the robot (1) is used to house a power source (69), the control means (60), transmitter and other peripherals required of an autonomous system.

According to the present invention, the distal end of the robot (1) is steerable to facilitate inspection and direction of advancement. Miniature motors may be used to activate a steering mechanism (15) embedded in the front two segments (2), and the steerable mechanism is driven by shape memory alloy wires.

The locomotion aspects of the present invention may be applied in any elongated passage having an elastic or rigid, tubular wall. Although only two embodiments have been shown and described, it would be obvious to those skilled in the art that many modifications to the present robot (1) is possible without departing from the spirit and scope of our invention.

What is claimed is:

1. A robotic endoscope for performing endoscopic procedures in a tubular organ comprising:
   (a) a plurality of segments, connected together by a plurality of flexible articulated joints, having a distal end;
   (b) a plurality of flexible linear actuators attached circumferentially around each segment, each of said linear actuators including a portion that is extendible and retractable along a longitudinal axis of that linear actuator, wherein the longitudinal axis of each linear actuator is skewed sideways with respect to the longitudinal axis and diametrical axis of each respective segment;
   (c) a central cavity running longitudinally through said robotic endoscope which houses a plurality of optical fibers, a water/air hose, an instrumentation channel and a plurality of electrical wires associated with an imaging means being mounted at the distal end; and
   (d) a network of tributary channels for the distribution of pressure to said linear actuators.

2. The robotic endoscope of claim 1, wherein said articulated joints connecting the segments possess three passive degrees of freedom to allow the robotic endoscope to conform to different curvatures.

3. The robotic endoscope of claim 1, wherein the plurality of linear actuators are rubber bellows.

4. The robotic endoscope of claim 1, wherein the linear actuators are driven by pneumatics or hydraulics.

5. The robotic endoscope of claim 1, further comprising a control means for implementing a plurality of gaits relating to speed, and ability to advance against gravity or ability of advance through difficult bends.

6. The robotic endoscope of claim 1, wherein the distal end of the segments is steered by lead wires connected to an electric motor.

7. The robotic endoscope of claim 1, wherein the distal end of the segments is steered by lead wires connected to a plurality of shape memory alloy wires.

8. The robotic endoscope of claim 1, wherein the linear actuators are padded at the tips of the bellows.

9. The robotic endoscope of claim 1, wherein tone imaging means is a charge couple camera.

10. The robotic endoscope of claim 1, wherein the segments are cylindrical.

11. An autonomous robot capable of advancing in pipes of small diameters comprising:
   (a) a plurality of segments, connected together by a plurality of flexible articulated joints, having a distal end;
   (b) a plurality of electrically (pneumatically or hydraulically) driven linear actuators attached circumferentially around each segment, each of said linear actuators including a portion that is extendible and retractable along a longitudinal axis of that linear actuator, wherein the longitudinal axis of each linear actuator is skewed sideways with respect to the longitudinal axis of each respective segment;
   (c) a central cavity running longitudinally through the robot which houses a power source, a control means, and a transmitter for an autonomous robot.

12. The autonomous pipe robot of claim 11, wherein the plurality of the articulated joints connecting the segments possess three degrees of freedom to allow the robot to conform to different curvatures.

13. The robotic endoscope of claim 11, further comprising a control means for implementing a plurality of gaits relating to speed, ability to advance against gravity or ability of advance through difficult bends.

14. The autonomous pipe robot of claim 11, wherein said distal end of the segments is steered by a miniature motor.

15. The autonomous pipe robot of claim 11, wherein said distal end of the segments is steered by shape memory alloy wires.

16. The autonomous pipe robot of claim 11, wherein an imaging means is mounted at the distal end of the segments.

17. The autonomous pipe robot of claim 16, wherein the imaging means is a charge couple camera.

18. The autonomous pipe robot of claim 11, wherein the linear actuators are swivellable to an opposite direction to facilitate backwards propulsion.

19. The autonomous pipe robot of claim 11, wherein the plurality of segments are rigid and cylindrical in shape.

20. The autonomous pipe robot of claim 11, wherein the plurality of linear actuators are rubber bellows.

* * * * *